United States Patent
Westmoreland et al.

(10) Patent No.: US 9,347,848 B1
(45) Date of Patent: May 24, 2016

(54) MARINE PROBE WITH NO MOVING PARTS FOR A MARINE TANK

(71) Applicant: INNOVATIVE MEASUREMENT METHODS, INC., Sugar Land, TX (US)

(72) Inventors: Allen Ray Westmoreland, Sugar Land, TX (US); John Charles Hoben, Sugar Land, TX (US); Alexander Bukhman, Sugar Land, TX (US); Yosef Brodsky, Sugar Land, TX (US)

(73) Assignee: INNOVATIVE MEASUREMENT METHODS, INC., Sugar Land, TX (US)

( * ) Notice: Subject to any disclaimer, the term of this patent is extended or adjusted under 35 U.S.C. 154(b) by 0 days.

(21) Appl. No.: 15/041,847

(22) Filed: Feb. 11, 2016

(51) Int. Cl.
| | | |
|---|---|---|
| G06F 17/00 | (2006.01) | |
| G01L 19/00 | (2006.01) | |
| G01N 9/26 | (2006.01) | |
| G01N 25/00 | (2006.01) | |
| G01L 7/08 | (2006.01) | |
| G01N 33/28 | (2006.01) | |
| G01G 17/04 | (2006.01) | |
| G01C 9/02 | (2006.01) | |
| G01F 23/00 | (2006.01) | |

(52) U.S. Cl.
CPC .............. *G01L 19/0092* (2013.01); *G01C 9/02* (2013.01); *G01F 23/0061* (2013.01); *G01G 17/04* (2013.01); *G01L 7/08* (2013.01); *G01N 9/26* (2013.01); *G01N 25/00* (2013.01); *G01N 33/2847* (2013.01)

(58) Field of Classification Search
CPC ......... G01S 5/0027; G01S 19/49; H04Q 9/00; H04Q 2209/10; H04Q 2209/82; H04Q 2209/40; G05B 23/0213; G05B 2219/13

USPC ..................... 702/50; 701/984, 612
See application file for complete search history.

(56) References Cited

U.S. PATENT DOCUMENTS

| | | | | | |
|---|---|---|---|---|---|
| 5,043,727 | A * | 8/1991 | Ito | ............................ | B63J 99/00 340/438 |
| 5,229,766 | A * | 7/1993 | Hargest | ................. | B63B 25/082 116/112 |
| 5,485,740 | A * | 1/1996 | Lippmann | ........... | G01F 25/0061 73/1.73 |
| 6,326,895 | B1 * | 12/2001 | Hartke | ................... | G01F 23/303 340/612 |
| 7,327,286 | B2 * | 2/2008 | Knoska | ................. | G01M 17/00 114/258 |
| 7,380,542 | B1 * | 6/2008 | Herrington | ........ | F02M 37/0088 123/509 |
| 7,426,014 | B2 * | 9/2008 | Sogard | ..................... | G03D 3/02 355/30 |
| 7,505,836 | B2 * | 3/2009 | Okuyama | ............... | F02B 77/08 340/438 |

(Continued)

*Primary Examiner* — Carol S Tsai
(74) *Attorney, Agent, or Firm* — Buskop Law Group, PC; Wendy Buskop

(57) ABSTRACT

A marine probe with no moving parts for use in one or more tanks on a floating vessel. The marine probe has pressure transducers, temperature sensors, an inclinometer, and a probe processor electrically connected to the pressure transducers, temperature sensors, inclinometer and a probe data storage. The marine probe controls the temperature sensors and pressure transducers to produce bidirectional signals and calculate at least one physical property, performs adaptive measurement for dynamic and static synchronized and non-synchronized measurement, identifies temperature sensors and pressure transducers not covered by the fluid, measures multiple parameters of the fluid in the tank, calibrates pressure transducers in a vapor space of the tank when the pressure transducers are no longer in the fluid, and creates bidirectional signals using values from the inclinometer transferring the bidirectional signals to a client device via a network.

18 Claims, 8 Drawing Sheets

(56) References Cited

U.S. PATENT DOCUMENTS

| | | | |
|---|---|---|---|
| 8,181,502 B2* | 5/2012 | Loodberg | B63B 11/04 73/1.73 |
| 8,594,866 B1* | 11/2013 | Chen | B60L 3/00 701/21 |
| 8,742,953 B1* | 6/2014 | Snyder | B63B 17/0036 340/612 |
| 8,996,210 B2* | 3/2015 | Kish | G05B 23/0213 701/21 |
| 2004/0149003 A1* | 8/2004 | Nestvall | G01F 25/0069 73/1.73 |
| 2005/0248444 A1* | 11/2005 | Joao | B60R 25/042 340/426.13 |
| 2009/0187297 A1* | 7/2009 | Kish | G05B 23/0213 701/21 |
| 2009/0260414 A1* | 10/2009 | Loodberg | B63B 11/04 73/1.73 |
| 2015/0246711 A1* | 9/2015 | Lee | B63B 21/50 405/224 |

* cited by examiner

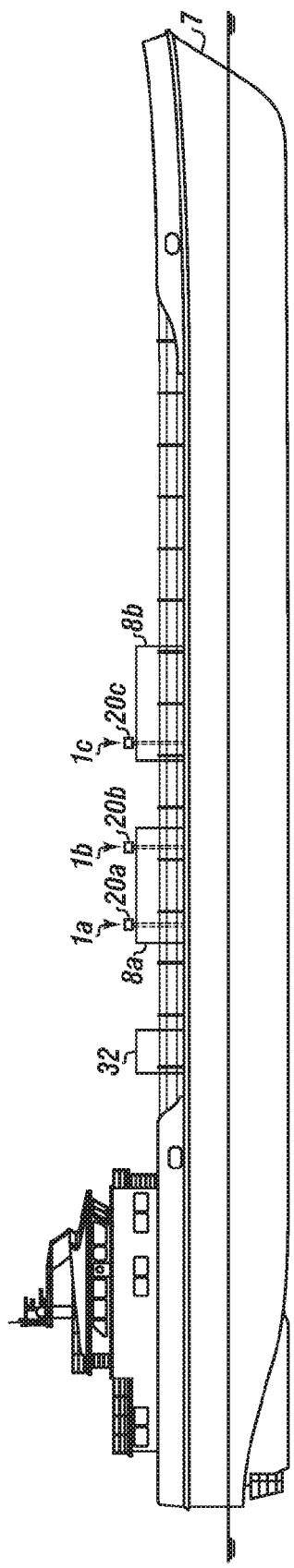

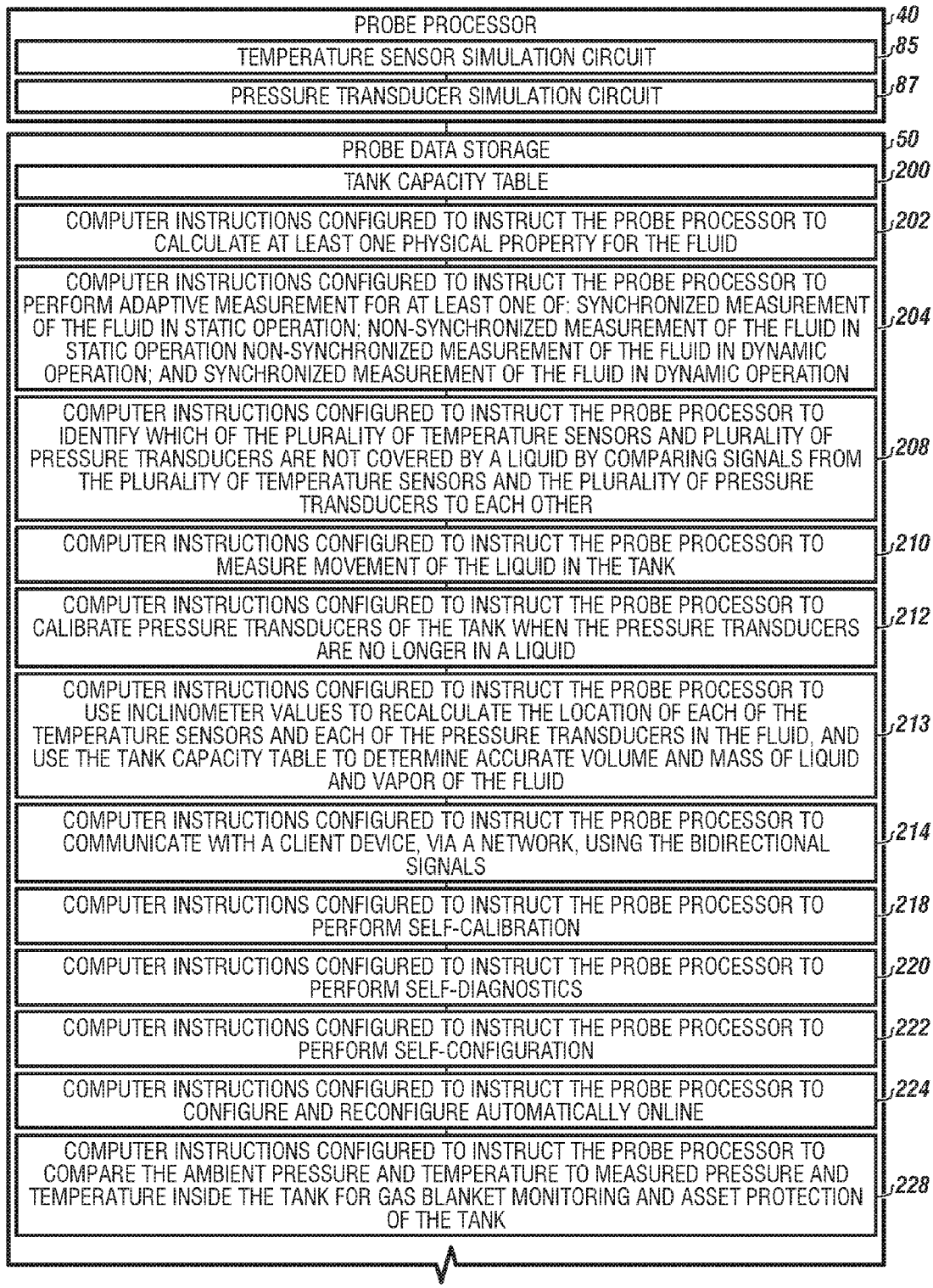

MARINE PROBE WITH NO MOVING PARTS FOR A MARINE TANK

FIELD

The present embodiments generally relate to a marine probe for measuring fluids in one or more tanks on a marine floating vessel.

BACKGROUND

A need exists for a highly sensitive monitoring probe for use on a floating vessel that is easy to manufacture, easy to install and incorporates the use of synchronized sensing devices for increase accuracy in measurements and can accommodate pitch, heave and yaw motions.

The present embodiments meet these needs.

BRIEF DESCRIPTION OF THE DRAWINGS

The detailed description will be better understood in conjunction with the accompanying drawings as follows:

FIG. 1A depicts a plurality of marine probes mounted to a floating vessel according to one or more embodiments.

FIGS. 5A and 5B depict a probe processor and a probe data storage according to one or more embodiments.

Figure 1B:
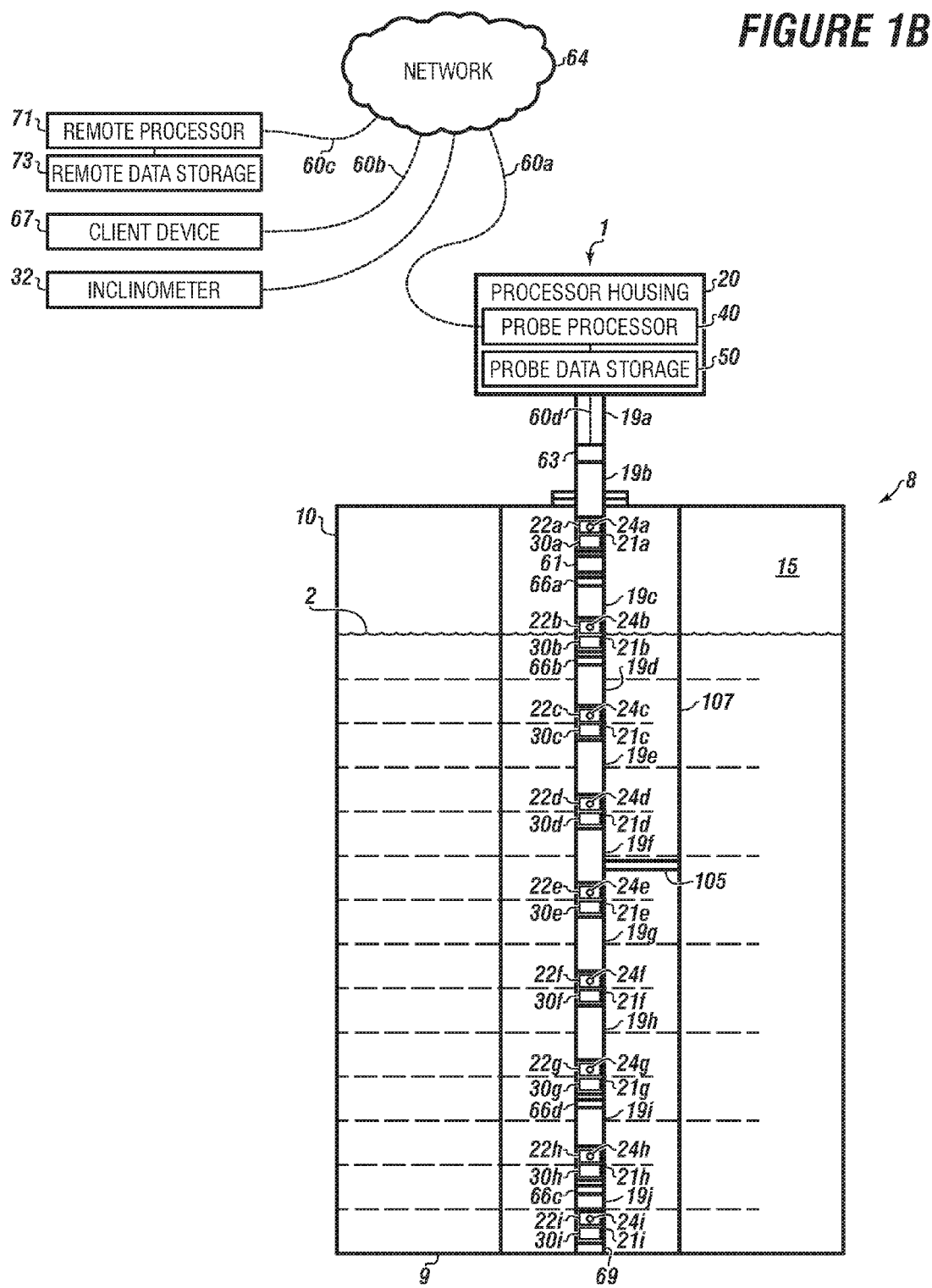
FIG. 1B shows a detail of a marine probe according to one or more embodiments.

The present embodiments are detailed below with reference to the listed Figures.

DETAILED DESCRIPTION OF THE EMBODIMENTS

Before explaining the present apparatus and system in detail, it is to be understood that the apparatus and system are not limited to the particular embodiments and that it can be practiced or carried out in various ways.

The embodiments relate to a marine probe with no moving parts for use in one or more tanks of a floating vessel, such as ships, barges and offshore floating platforms In embodiments, the marine probe can be connected with other marine probes and be operable from a remote control processor connected through a network.

The marine probe can have a plurality of pressure transducers and a plurality of temperature sensors electrically connected to a probe processor.

The marine probe controls the temperature sensors and pressure transducers to produce bidirectional signals and calculates at least one physical property of fluid in the tank while performing adaptive measurement for dynamic and static synchronized and non-synchronized measurement.

The marine probe additionally identifies temperature sensors and pressure transducers not covered by the fluid in the tank.

The marine probe can calibrate pressure transducers in a vapor space of the tank when the pressure transducers are no longer in the fluid and can use values from an inclinometer transferring the bidirectional signals to a client device via a network to provide accurate interpretations of pressure measurements.

The present embodiments can have the benefit of being both a leak detection and an emission monitoring apparatus that can both detect leaks and monitor emissions from tanks of floating vessels, and then perform, automatically, using a probe processor or a remote processor, a comparison of measured emission to stored requirements of environmental laws and regulations which can be stored in a data storage connected to the processor, and then automatically provide a notification via a network to a client device when the comparison fails to comply with the stored requirements of environmental laws and regulations.

The present embodiments are for a marine probe that can utilize multiple temperature sensors and multiple pressure transducers for performing hydrostatic tank measurements and provide increased accuracy and consistence with regard to measurement values.

Specific structural and functional details disclosed herein are not to be interpreted as limiting, but merely as a basis of the claims and as a representative basis for teaching persons having ordinary skill in the art to variously employ the present embodiments.

The term "fluid" as used herein can include liquids, gasses with or without particulates and combinations thereof. Vapor pressure can be used in the conventional manner and can be included within the scope of the term "gas" for this application. Fluids include hydrocarbons, water, gasoline, oil, pharmaceuticals, alcohols, esters, inert gasses and vapors.

The term "fluid temperature" as used herein can refer to an average fluid temperature or a multipoint spot temperature of the fluid.

The term "inclinometer" as used herein can refer to an instrument for measuring angles of a floating object with respect to gravity. The inclinometer can measure after draft, forward draft, list, trim, or pitch and roll.

The term "pressure transducer" as used herein can refer to a device that measures pressure of the fluid.

The term "processor" as use herein can be a laptop, a cellular phone or smart phone, a desktop computer, a server on a network, an additional measuring device that does different measuring and can connect to the plurality of temperature sensors and plurality of pressure transducers, and combinations thereof. The processor can be in wired or wireless communication with the temperature sensors and pressure transducers.

The term "data storage" refers to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals.

The term "simultaneously' as used herein can mean the temperature sensors and pressure transducers can collect measured data at the same time or within a few milliseconds of each other, such as a period ranging from zero to one hundred milliseconds.

The term "temperature sensor" as used herein can refer to either one temperature sensor, or a pair of temperature sensors for detecting a temperature of a fluid in a tank.

The term "tank" as used herein can refer to a wide variety of tanks, and containers that hold fluids including separators, storage tanks, container trucks, vats. For example, the tank can include a tank containing as much as ten barrels of oil, or as much as 1,000,000 barrels of oil. The tank can be structured with or without floating roofs. The tank can have any shape, including circular shapes, square shapes or other similar shapes. Tanks of any volume made from various materials are contemplated.

The marine probe of the invention can occupy less space than other attachment methods.

The marine probe of the invention can provide the benefit of continuous measurements, while providing a comparison of measured values with preset limits, such as environmental standards.

The marine probe of the invention can provide enhanced accuracy and consistent measurement over existing detection and monitoring apparatus.

The versatile marine probe of the invention can identify many physical characterizes that can be measured using the temperature sensors and pressure transducers for the gas, liquid, with or without particulate matter.

Use of the present marine probe of the invention can prevent hazardous environmental emissions, and avoid other potentially dangerous or detrimental fluid conditions through continuous monitoring.

The comparison of measurements with preset limits by the marine probe as described herein, can allow remediation to be taken when fluid conditions reach unacceptable levels, such as extreme pressures and temperatures, the formation of vacuums, and the emissions of harmful amounts of hydrocarbons and other potentially harmful chemicals, thereby preventing environmental contamination, explosions, loss of fluid, death and damage to equipment.

For example, a calculated value, such as a mass of a fluid can range from a few tons to hundreds of thousands of tons of crude oil in a ship or barge. A calculated value, such as a fluid volume in a tank can range from tens of barrels to millions of barrels of liquid petroleum gas. Fluid density can range from 0.5 g/cm$^3$ to 2 g/cm$^3$ or more for most petroleum products. Temperature of the fluid can range from −60 degrees Centigrade to 200 degrees Centigrade and can include vapor temperatures in addition to liquid temperature measurement. Impurity of the fluid can include a detection of water in oil on a percentage basis, such as a 5 percent impurity in West Texas crude oil.

The marine probe can communicate via a network with a remote processor to use a computed mass of the fluid for balancing a floating vessel during loading, and unloading of the floating vessel; and for inventory control and custody transfer.

In an embodiment, one or more of the pressure transducers can include a diaphragm. The diaphragm can be oriented horizontal to the bottom of the tank but can be at other orientations.

In embodiments, one or more of the temperature sensors or pressure transducers can provide an analog signal to a probe processor. The analog signal can be digitized, such as by use of an analog-to-digital converter, and stored in fixed or removable data storage, transmitted to remote data storage or another processor, or combinations thereof.

In embodiments, the marine probe can use temperature sensors and pressure transducers with a built-in processor and direct digital communications to probe processor. That is, each temperature sensors and pressure transducer can communicate with a probe processor which then can wirelessly communicate or make a wired connection to a network with a remote processor and remote data storage, such as a cloud processing system.

A particular example of the marine probe can contemplate using temperature sensors and pressure transducers in a long row, each temperature sensor and pressure transducers having a sequential number 1 to 10. In this embodiment, the temperature sensors numbering 1, 3, 5, 7, 9 can communicate with a processor "A" the temperature sensors with numbers 2, 4, 6, 8, and 10 can communicate with a processor "B". This alternating measurement using multiple processors continuously can provide for the extreme high accuracy and reliability of measurement with this device.

By connecting multiple probes of the probe processor together, the individual marine probe data can be compounded to create a virtual reading within one tank in case multiple probes are installed into the same tank.

The synchronization of the pressure transducers can be established using a clock or timed device with the processor or internal to the processor, to synchronize pressure transducers, electronic switches and signals, analog-to-digital converters, and other equipment connected to the invention for increased accuracy.

The probe processor can synchronously poll measurement data from the one or more temperature sensors and one or more pressure transducers to simultaneously and continuously calculate values, forming calculated values. For example, the fluid density can be difficult to measure in a moving fluid without using synchronized data.

The probe processor can convert pressure and temperature sensor data to one or more values using computer instructions with models and other computations stored in memory of the associated data storage. The values can provide a reading or notification of a measurement or leak detection and related measurement, including unauthorized movement of fluid from the tank.

The calculated values can be compared to one or more predetermined ranges of values for the fluid to identify whether the calculated values are within the predetermined ranges. For example, a density of a specific crude oil can have a predetermined range from 0.85 to 1.0 g/cm$^3$ and the present apparatus can constantly collect data and compare the collected data to that predetermined range. It can be contemplated that notification can be provided if the calculated values exceed a predetermined range. Use of automated responses, such as alarms, when the calculated values exceed a predetermined range, can also be contemplated.

The calculated values can include a mass of the fluid, a fluid volume, an average temperature of the fluid, a multiple density strata of the fluid, an average density of the fluid, a level of the fluid, a fluid flow rate, an impurity content of the fluid, an entrained water content of the fluid, a free water content of the fluid, or combinations thereof.

An embodiment of the invention can monitor and compare measurements for atmospheric or ambient pressures and temperatures to measure for vapor pressures and vapor temperatures to provide data simultaneously with notifications and/or alarms. Examples of these types of data can include extreme pressures, extreme temperatures, formation of vacuums, high amounts of hydrocarbon emissions or other harmful chemical emissions, or combinations thereof. Immediate notifications and alarms can be produced to provide an alert of potentially harmful gasses, liquids, and vapors that are escaping into the atmosphere and surrounding area.

The probe processor can communicate compared values to a data collector, which can include one or more data storage media in communication with the processor, including remote data storage media, removable data storage media, and fixed data storage media.

In embodiments, the remote processor can communicate with one or more of the following: (1) a remote terminal unit, such as a Bristol Babcock RTU for tubular line monitoring, (2) a distributive control system, such as, a Honeywell DSC 3000, (3) a supervised control and data acquisition (SCADA) system, such as a Human Machine Interface system, (4) another computer, (5) another a tank or vessel gauge interface unit, such as a 1515 ETGI provided by Gauging Systems, Inc., of Houston, Tex., and other similar devices.

In embodiments, communication of compared values to the remote processor can be performed using a field wiring bus, a network, or combinations thereof. Useable networks can include the internet, a local area network, a radio network, a hard wired network, a copper wire network, a cellular network, a satellite network, a fiber optic network, an infrared connection, a plain old telephone system (POTS), other wireless or wired networks, and combinations thereof.

In an embodiment, temperature sensors and pressure transducers can each include a transmitter, such as a radio transceiver, a satellite transmitter, a cellular transceiver, an RS-485 wired transmitter, or other similar transmitters. The transmitter can communicate between the temperature sensors and pressure transducers and the remote processor. In embodiments, communication can be a wireless communication, such as an infrared, satellite, or cellular communication, a fiber optic communication, a cabled communication, or combinations thereof.

In embodiments, a transmitter can be disposed in proximity to one or more tanks for transmitting data from the temperature sensors and pressure transducers within the one or more tanks to a remote processor.

The invention can include a sensor housing for containing temperature sensors and pressure transducers. The sensor housing can be made from any durable material, including machined stainless steel, plastic, a metal alloy, such as HASTELLOY-C™, TEFLON™, aluminum, KYNAR™ composites, ceramic composites, and formed polymer blends, such as PVC.

In an embodiment, the invention can include one or more channels. The channels can contain signaling wires to convey temperature sensor data to the probe processor. The channels can be smooth walled. The signaling wires can be multiconductor wire, such as wire available from Belden, other types of wire, or similar communication wiring, such as fiber optic wiring or cable.

In one embodiment, the invention can be installed into or in proximity to a gauge well or gauge hatch of a large tank, such as an oil tank, on a floating vessel, so that uncertainties caused by comparison with manual gauging due to reference point movement or bottom movement of the tank are eliminated.

By locating the invention with the gauge well of the tank, the invention can provide multiple measurements at the same single location where manual measurements are taken and greatly increase the verifiability of a monitoring function.

With this alignment, the invention can measure automatically all the values that are measured manually from the gauge well so that comparisons can be made of many variables at the same time the manual samplings by the gauge well are occurring.

Examples of samplings and measurement values can include: a fluid level, temperatures of the fluid, fluid density, and a percentage of water content in a hydrocarbon fluid.

Tank samplings and measured values include: level and temperature of the fluid and fluid density. The alignment of the invention with the gauge well of the tank can allow the measured values from the invention to be compared and calculated with the manual gauge well samplings and readings and dramatically improves the verification ability and consistency of the measurement values.

Turning now to the Figures, FIG. 1A shows a plurality of marine probes mounted on a floating vessel.

The plurality of marine probes 1a-1c can be mounted in tanks 8a-8b of the floating vessel 7. The tanks 8a-c can be mounted to a floating vessel 7. The floating vessel is depicted as a ship in this Figure. The floating vessel can also be a barge, a workboat, a floating offshore platform, such as an FPSO or the like. In embodiments, the floating vessel can be a submerged buoy. Each of the marine probe 1a-1c has no moving parts The plurality of marine probes 1a-1c can each have a processor housings 20a-20c.

An inclinometer 32 can be mounted to the floating vessel 7. The inclinometer 32 measures angles of the floating vessel relative to gravity.

FIG. 1B shows a detail of a marine probe according to one or more embodiments

The inclinometer 32 can be in communication with a network 64 and the probe processor 40.

A remote processor 71 can be connected to the network 64 having a remote data storage 73, which can also provide information to the probe processor.

A client device 67 is shown connected to the network for receiving information from the remote processor and/or the probe processor as needed for management and alerts of leak detection or any notifications including those related to floating vessel transit, loading and offloading of fluid.

The marine probe 1 can communicate to the network 64 using bidirectional signals 60a-60d and with the inclinometer 32.

The marine probe 1 can have a processor housing 20 configured to prevent degradation in marine environments, such as salt water. The processor housing 20 can be mounted outside of a tank 8.

Each tank in which the marine probe is mounted can have a floor 9 and at least one wall 10. In this Figure, the tank 8 is shown with a cylindrical wall.

The marine probe 1 can be configured for continuous measurement of a fluid 2 while immersed in that fluid. The fluid can be a combination of liquid and vapor. The tank 8 can have a vapor space 15 above the fluid 2 in the tank 8.

The marine probe 1 can have a plurality of pressure transducers 22a-22i, wherein each pressure transducer can have a diaphragm 24a-24i.

Each pressure transducer can be configured for continuous pressure measurement through direct contact with the fluid 2 in the tank 8.

The marine probe 1 can have a plurality of temperature sensors 30a-30i, wherein each of the temperature sensors can be contained in either one of the pressure transducers 22a-22i or in one of the sensor housings 21a-i.

Each temperature sensor can be configured for continuous temperature measurement of the fluid 2 in the tank 8.

The probe processor 40 can be in the processor housing 20. The probe processor can be electrically connected to the plurality of pressure transducers and to the plurality of temperature sensors and electronically connected to the network 64 with the bidirectional signals 60a-60d.

A probe data storage 50 can also be in the processor housing 20. The probe data storage can be in bidirectional communication with the probe processor.

The probe data storage can be a computer readable medium with computer instructions for instructing the probe processor to control the plurality of temperature sensors and plurality of pressure transducers and to produce bi-directional signals to the network as well as produce bidirectional signals to the plurality of temperature sensors and the plurality of pressure transducers.

A temperature and pressure transducer 61 can be located in the vapor space 15 of the tank 8. In embodiments, more than one temperature and pressure transducer can be used.

A plurality of conduits 19a-19j can connect to the processor housing 20 with the sensor housings 21a-21i. The plurality of conduits can extend to a bottom or the floor of the marine probe, and in embodiments, the bottom of the marine probe can be proximate or within inches, such as 1 inch to 30 inches of the floor 9 of the tank 8.

A plurality of switches 66a-66d are shown in the tank 8, wherein each switch can detect liquid levels, compare detected liquid levels to a preset level stored in the switch and then provide a notification signal to the client device 67 via the network, or a notification to the probe processor 40 or to both devices simultaneously, when liquid exceeds or fails to meet the preset level of the switch.

An external sensor 63 can be disposed outside of the tank 8. The external sensor can be electrically connected to the probe processor.

The external sensor 63 can be configured to measure ambient pressure and ambient temperature outside the tank.

The external sensor 63 can provide signals to the probe processor. The probe processor can use computer instructions in the probe data storage to compare the ambient pressure and temperature measured outside the tank by the external sensor to measured pressure and temperature inside the tank measured by the plurality of pressure transducers and the plurality of temperature sensors for gas blanket monitoring and asset protection of the tank 8.

The marine probe 1 can communicate using the bidirectional signals 60a with the network 64. Some of the bidirectional signals further transmit to the client device 67, wherein commands and data can be transmitted from the client device 67 to the network 64 for transmission to the probe processor 40.

In embodiments, the plurality of transducers, the plurality of temperature sensors, the plurality of conduits, the plurality of switches, the diaphragms and the sensor housings can be contained in an in tank housing 107 of the probe.

In embodiments, a spacer 105 can be used to keep the plurality of transducers, the plurality of temperature sensors space apart from the in tank housing 107. In embodiments, a plurality of spacers can be used.

In embodiments, the spacer can help stabilize the probe and prevent the marine vessel from listing.

At least one compound containing sulfur detector 69 can be used in the tank. In embodiments, the compound containing sulfur detector 69 can be in communication with the probe processor 40 for detecting compounds containing sulfur. In embodiments, the compound containing sulfur detector can be mounted in the vapor space 15 of the tank.

The probe processor can use computer instructions in the probe data storage configured to instruct the probe processor to compute compounds containing sulfur concentrations for protection of personnel or for estimation of quality of crude oil. The compounds containing sulfur detector can be in fluid in the tank, in the vapor space in the tank or mounted external to the tank.

Figure 2:
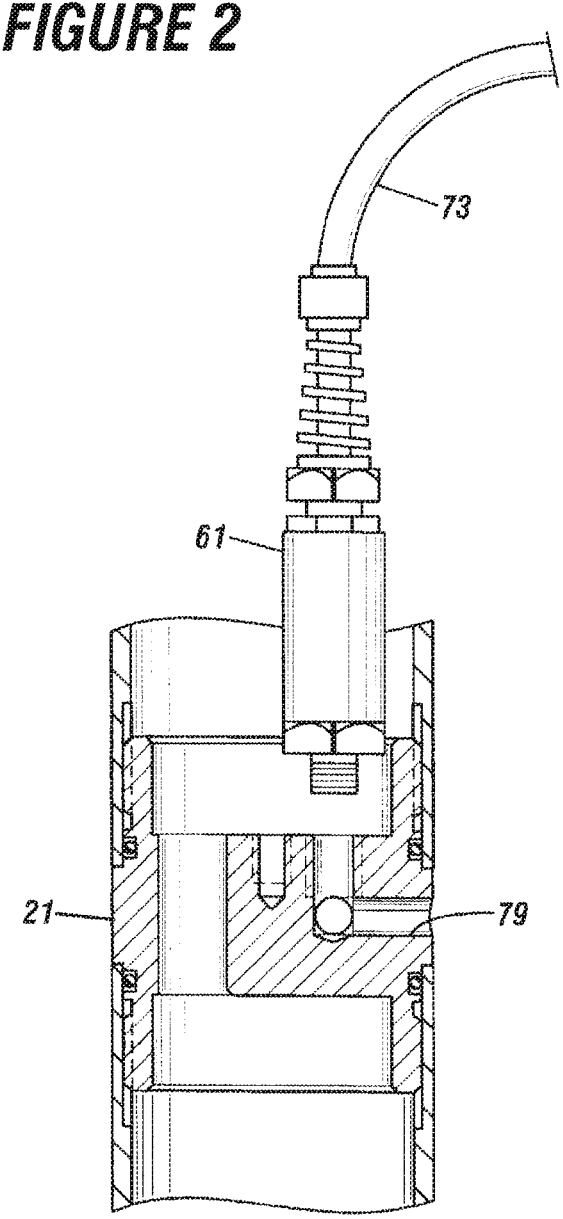
FIG. 2 shows a detail of sensor housing in partial cross section according to one or more embodiments.

FIG. 2 shows a detail of the sensor housing 21 in partial cross section according to one or more embodiments.

Output leads 73 are shown from a temperature and pressure transducer 61. The temperature and pressure transducer 61 can be disposed partially in the sensor housing 21. In embodiments, to operate the temperature and pressure transducer 61, a portion of the temperature and pressure transducer can be external of the sensor housing.

A channel 79 can be formed in the sensor housing 21. In embodiments, the channel 79 can have a plurality of inclined surfaces that can enable fluid from the tank to contact with the temperature and pressure transducer 61.

Figure 3:
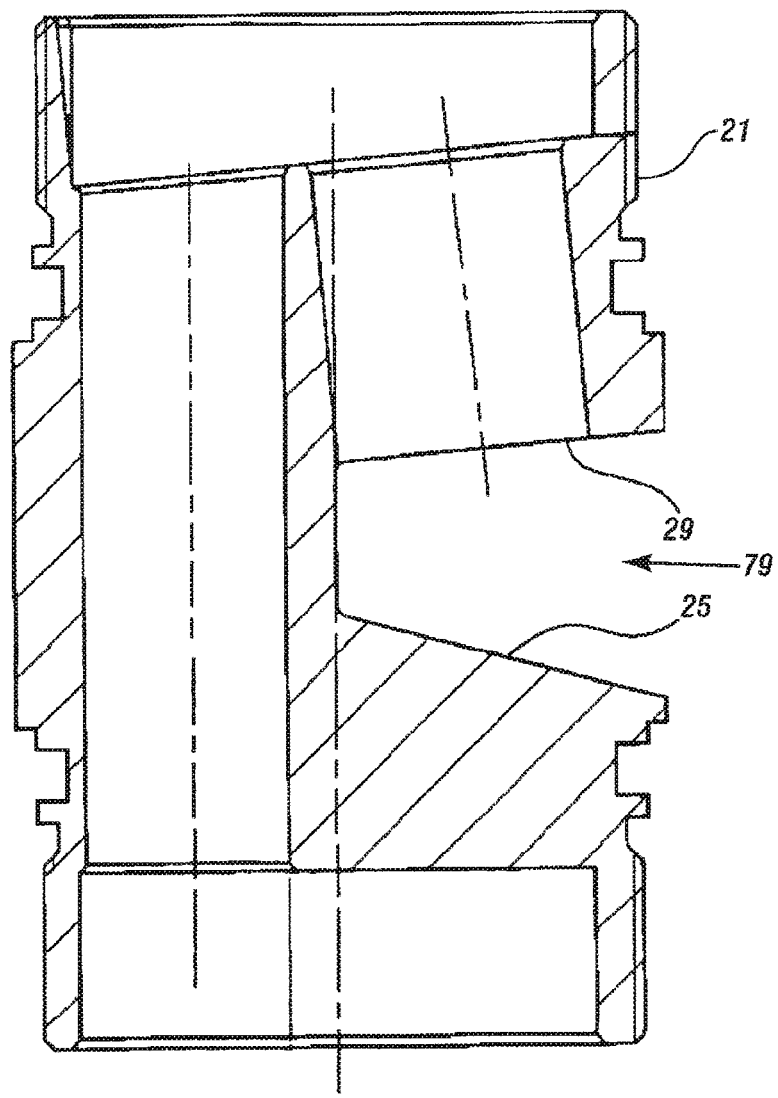
FIG. 3 is a detailed view of a sensor housing of a marine probe according to one or more embodiments.

FIG. 3 is a detailed view of a sensor housing of a marine probe according to one or more embodiments.

The channel 79 is shown in the sensor housing 21 of the marine probe. In this embodiment, the marine probe can have two inclined surfaces in the sensor housing, shown here as a first surface 25 and a second surface 29, which can form the channel 79. Each inclined surface can have a slope from 2 degrees to 50 degrees.

In embodiments, a plurality of inclined surfaces can be used on one side of the channel 79. The channel 79 can enable fluid from the tank to contact a pressure transducer or a temperature sensor in the sensor housing or a combination pressure and sensor transducer in the sensor housing.

In embodiments, just one inclined surface can be formed on a side of channel 79.

Figure 4:
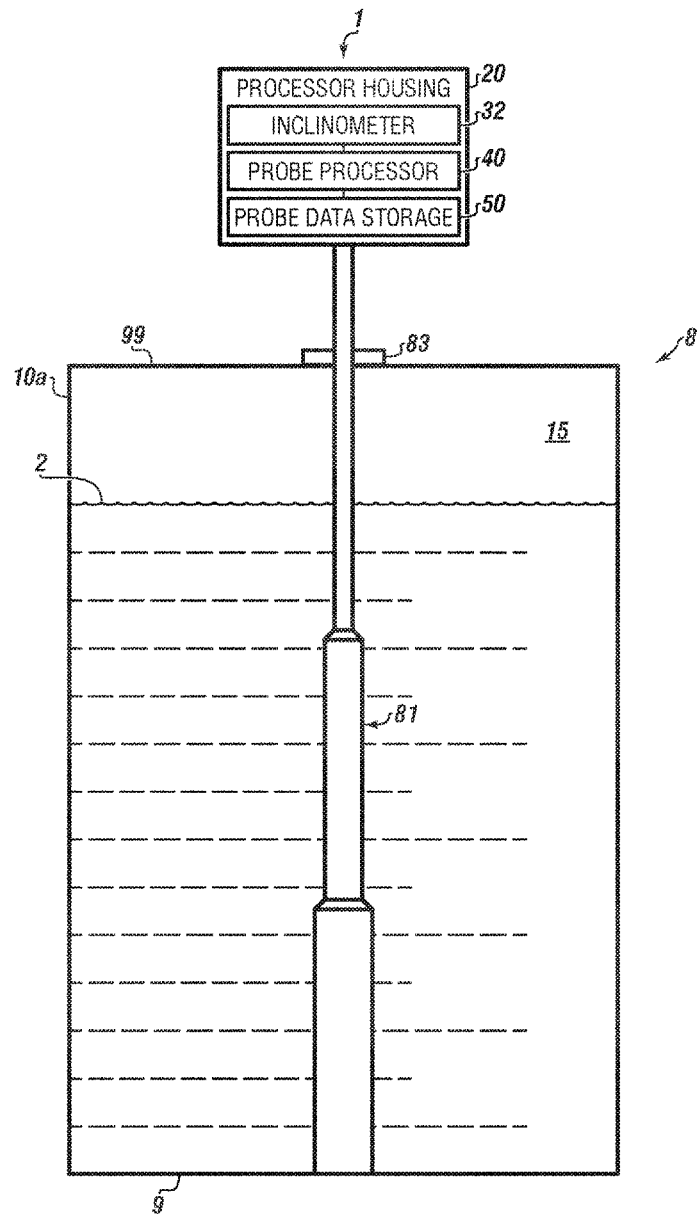
FIG. 4 shows a marine probe with an outer surface in a stepped configuration according to one or more embodiments

FIG. 4 shows a marine probe with an outer surface in a stepped configuration according to one or more embodiments The marine probe 1 is shown with an outer surface 81 formed in a sequential stepped configuration as three segments, wherein each segment expands at least 10 percent in diameter sequentially from an adjacent segment.

The marine probe 1 can have a tank movement measuring device 83 connected to a roof 99 of the tank 8 with the fluid 2 and the vapor space 15. The tank 8 can have at least one wall 10, shown here as a cylindrical tank, and a floor 9. The tank movement measuring device 83 can be mounted external of the tank 8.

The tank movement measuring device 83 can be electronically connected to the probe processor 40 in the processor housing 20 or the remote processor via the network. The tank movement measuring device can provide signals that can be stored in the remote processor data storage. The tank movement measuring device 83 can communicate with the probe processor 40 or a display for an operator. The tank movement measuring device can measure and display movement due to flexing of the floor 9 of the tank 8 or due to flexing of the roof 99 of the tank 8. The display can be a local display, a remote display, or combinations thereof.

The tank movement measuring device 83 can measure when the probe has moved due to the flexing of the floor 9 of the tank 8 with the fluid 2 or flexing of the roof 99 of the tank with the vapor space 15 relative to the floor 9. The tank movement measuring device can transmit those measurements to the probe data storage 50 either wirelessly or in a wired communication for further notification to the display associated with the probe processor 40 or the remote processor via the network or the client device via the network.

Figure 5B:
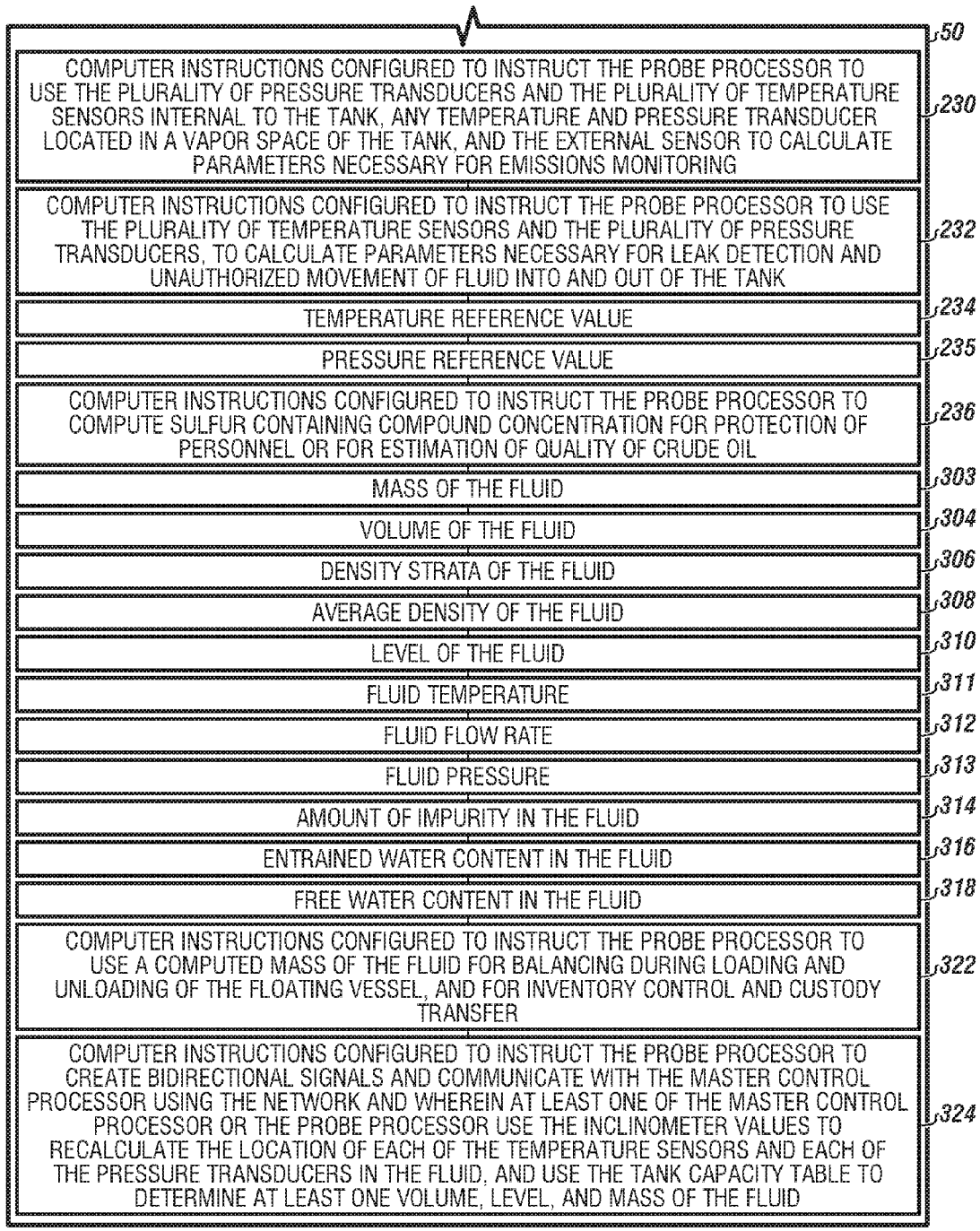

FIGS. 5A and 5B depict a probe processor and a probe data storage according to one or more embodiments.

In embodiments, the probe processor 40 can have a temperature sensor simulation circuit 85 and a pressure transducer simulation circuit 87.

The probe data storage 50 can be connected to the probe processor 40.

The temperature sensor simulation circuit 85 can be for automatically calibrating the probe processor and can use a temperature reference value 234 for calibration. The temperature reference value 234 can be shown in the probe data storage 50.

The pressure transducer simulation circuit 87 can be for automatically calibrating the probe processor. The pressure transducer simulation circuit can use a pressure reference value 235 for calibration. The pressure reference value 235 can be shown in the probe data storage 50.

The probe data storage 50 can contain a tank capacity table 200, which can show capacities and/or volumes in a tank for various fluid levels as measured from a reference gauge point.

The probe data storage can contain computer instructions 202 configured to instruct the probe processor to calculate at least one physical property for the fluid.

The physical properties can be stored in the probe data storage and can include but are not limited to: a mass of the fluid 303, a volume of the fluid 304, a density strata of the fluid 306, an average density of the fluid 308, a level of the fluid 310, a fluid temperature 311, a fluid flow rate 312, a fluid pressure 313, an amount of impurity in the fluid 314, an entrained water content in the fluid 316, and a free water content in the fluid 318.

The probe data storage can contain computer instructions 204 to instruct the probe processor to perform adaptive measurement for at least one of: synchronized measurement of the fluid in static operation, non-synchronized measurement of the fluid in static operation, non-synchronized measurement of the fluid in dynamic operation, and synchronized measurement of the fluid in dynamic operation.

The probe data storage can contain computer instructions 208 configured to instruct the probe processor to identify which of the plurality of temperature sensors and the plurality of pressure transducers are not covered by a fluid by comparing signals from the plurality of temperature sensors and the plurality of pressure transducers to each other.

The probe data storage can contain computer instructions 210 configured to instruct the probe processor to measure movement of the fluid in the tank.

The probe data storage can contain computer instructions 212 configured to instruct the probe processor to calibrate pressure transducers of the tank when the pressure transducers are no longer in a fluid.

The probe data storage can contain computer instructions 213 configured to instruct the probe processor to use inclinometer values to recalculate the location of each of the temperature sensors and each of pressure transducers in the fluid, and use the tank capacity table to determine accurate volume and mass of liquid and vapor of the fluid.

The probe data storage can contain computer instructions 214 configured to instruct the probe processor to communicate with a client device via a network by using the bidirectional signals.

The probe data storage can contain computer instructions 218 configured to instruct the probe processor to perform self-calibration.

The probe data storage can contain computer instructions 220 configured to instruct the probe processor to perform self-diagnostics.

The probe data storage can contain computer instructions 222 configured to instruct the probe processor to perform self-configuration.

In embodiments, the probe data storage can have at least one computer instruction configured to instruct the probe processor to preform self-calibration, perform self-diagnostics, perform self-configuration, or various combinations thereof.

The probe data storage can contain computer instructions 224 configured to instruct the probe processor to configure and reconfigure automatically online.

The probe data storage can contain computer instructions 228 configured to instruct the probe processor to compare the ambient pressure and temperature to measured pressure and temperature inside the tank for gas blanket monitoring and asset protection of the tank.

The probe data storage can contain computer instructions 230 configured to instruct the probe processor to use the plurality of pressure transducers and temperature sensors internal to the tank, any temperature and pressure transducer located in a vapor space of the tank and the external sensor to calculate parameters necessary for emissions monitoring.

The probe data storage can contain computer instructions 232 configured to instruct the probe processor to use the plurality of temperature sensors and/or the plurality of pressure transducers to calculate parameters necessary for leak detection and unauthorized movement of fluid into and out of the tank.

The temperature sensor simulation circuit's temperature reference value 234 and the pressure transducer simulation circuit's pressure reference value 235 are shown in the probe data storage 50.

The probe data storage can contain computer instructions 236 configured to instruct the probe processor to compute sulfur containing compound concentration for protection of personnel or for estimation of quality of crude oil as mentioned earlier.

The probe data storage can contain computer instructions 322 configured for instruct the remote processor to use a computed mass of the fluid for balancing during loading and unloading of the floating vessel and for inventory control and custody transfer.

Figure 6:
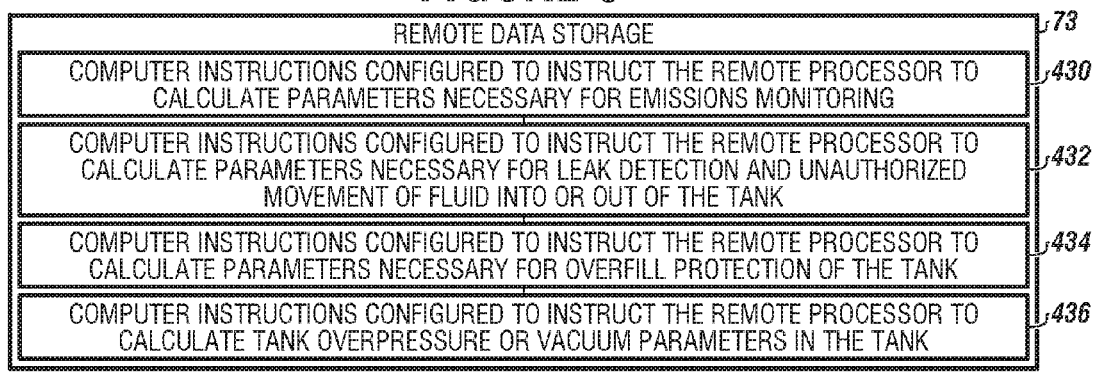
FIG. 6 depicts a remote data storage according to one or more embodiments.

FIG. 6 depicts a remote data storage according to one or more embodiments.

The remote data storage can contain computer instructions 430 configured to instruct the remote processor to calculate parameters necessary for emission monitoring.

The remote data storage can contain computer instructions 432 configured to instruct the remote processor to calculate parameters necessary for leak detection and unauthorized movement of fluid into or out of the tank.

The remote data storage can contain computer instructions 434 configured to instruct the remote processor to calculate parameters necessary for overfill protection of the tank.

The remote data storage can contain computer instructions 436 configured to instruct the remote processor to calculate tank overpressure or vacuum parameters in the tank.

In embodiments, the processor housing can be weatherproof or explosion proof.

In embodiments, at least one marine probe can be used. In embodiments, multiple or a plurality of marine probes can be used in one or more tanks of a floating vessel.

In embodiments, multiple probe processors and probe data storages can be used.

In an embodiment, a plurality of processor housings can be configured to prevent degradation in marine environments.

In embodiments, the inclinometer can be mounted to the floating vessel and can provide measuring angles of the floating vessel relative to gravity for use by each probe processor.

Each probe processor can electrically and bi-directionally connect to each of the plurality of pressure transducers, the plurality of temperature sensors and the inclinometer of the marine probe system.

While these embodiments have been described with emphasis on the embodiments, it should be understood that within the scope of the appended claims, the embodiments might be practiced other than as specifically described herein.

What is claimed is:

1. A marine probe with no moving parts for use in a tank of a floating vessel, the tank having a floor and at least one wall, the marine probe configured for continuous measurement of a fluid while immersed in the fluid, wherein the marine probe comprises:
   a) a processor housing configured to prevent degradation in marine environments;
   b) a plurality of sensor housings connected to the processor housing;
   c) a plurality of pressure transducers, each pressure transducer within a sensor housing, each pressure transducer having a diaphragm, each pressure transducer configured for continuous pressure measurement through direct contact with the fluid in the tank;
   d) a plurality of temperature sensors, each temperature sensor within a sensor housing or contained in each pressure transducer, each temperature sensor configured for continuous temperature measurement of the fluid in the tank;
   e) an inclinometer mounted to the floating vessel or within the processor housing for measuring angles of the floating vessel relative to gravity;
   f) a probe processor in the processor housing, the probe processor electrically and bidirectionally connected to the plurality of pressure transducers, to the plurality of temperature sensors, the inclinometer and a network; and
   g) a probe data storage in the processor housing, the probe data storage in communication with the probe processor, the probe data storage being a computer readable medium with computer instructions for instructing the probe processor to control the plurality of temperature sensors and the plurality of pressure transducers to produce bidirectional signals to the network, to the plurality of temperature sensors and to the plurality of pressure transducers, the probe data storage containing:
      (i) a tank capacity table;
      (ii) computer instructions configured to instruct the probe processor to calculate at least one physical property for the fluid, the physical property selected from the group consisting of:
         1) a mass of the fluid;
         2) a volume of the fluid;
         3) a density strata of the fluid;
         4) an average density of the fluid;
         5) a level of the fluid;
         6) a fluid temperature;
         7) a fluid flow rate;
         8) a fluid pressure;
         9) an amount of impurity in the fluid;
         10) an entrained water content in the fluid; and
         11) a free water content in the fluid;
      (iii) computer instructions configured to instruct the probe processor to: perform adaptive measurement for at least one of:
         1) a synchronized measurement of the fluid in static operation;
         2) a non-synchronized measurement of the fluid in static operation;
         3) a non-synchronized measurement of the fluid in dynamic operation; and
         4) a synchronized measurement of the fluid in dynamic operation;
      (iv) computer instructions configured to instruct the probe processor to identify which of the plurality of temperature sensors and the plurality of pressure transducers are not covered by the fluid by comparing signals from the plurality of temperature sensors and the plurality of pressure transducers to each other;
      (v) computer instructions configured to instruct the probe processor to measure movement of the fluid in the tank;
      (vi) computer instructions configured to instruct the probe processor to calibrate pressure transducers of the tank when the pressure transducers are no longer in the fluid;
      (vii) computer instructions configured to instruct the probe processor to use inclinometer values to recalculate the location of each of the temperature sensors and each of the pressure transducers in the fluid, and use the tank capacity table to determine accurate volume and mass of liquid and vapor of the fluid; and
      (viii) computer instructions configured to instruct the probe processor to communicate with a client device via the network using the bidirectional signals.

2. The marine probe of claim 1, comprising at least one temperature and pressure transducer located in a vapor space of the tank.

3. The marine probe of claim 1, wherein an outer surface of the marine probe expands in a stepped configuration, increasing at least ten percent in diameter.

4. The marine probe of claim 1, comprising a channel in the sensor housing to provide contact with the fluid from the tank to at least one of the plurality of temperature sensors and at least one of the plurality of pressure transducers.

5. The marine probe of claim 1, comprising a plurality of switches in the tank that provide a notification signal to the probe processor, the network, or both the probe processor and the network when the liquid exceeds or fails to meet a preset level.

6. The marine probe of claim 1, comprising a tank movement measuring device connected to at least one of: the probe processor and a remote processor for displaying and measuring marine probe movement due to flexing of the floor of the tank or due to flexing of a roof of the tank.

7. The marine probe of claim 1, wherein the probe data storage comprises at least one of:
   a) computer instructions configured to instruct the probe processor to perform self-calibration;
   b) computer instructions configured to instruct the probe processor to perform self-diagnostics; and
   c) computer instructions configured to instruct the probe processor to perform self-configuration.

8. The marine probe of claim 1, wherein the probe data storage comprises computer instructions configured to instruct the probe processor to configure and reconfigure online.

9. The marine probe of claim 4, comprising a plurality of inclined surfaces on at least one side of the channel, the plurality of inclined surfaces enabling fluid to contact with at least one of: a pressure transducer and a temperature sensor.

10. The marine probe of claim 1, comprising a temperature sensor simulation circuit in the probe processor with a temperature reference value in the probe data storage and a pressure transducer simulation circuit in the probe processor with a pressure reference value in the probe data storage, the temperature sensor simulation circuit and the pressure transducer simulation circuit for calibrating the probe processor.

11. The marine probe of claim 6, comprising a remote processor bidirectionally connected to the probe processor via the network, the remote processor further comprising a remote data storage, the remote data storage comprising at least one of:

a) computer instructions configured to instruct the remote processor to calculate parameters necessary for emissions monitoring;
b) computer instructions configured to instruct the remote processor to calculate parameters necessary for leak detection and unauthorized movement of fluid into or out of the tank;
c) computer instructions configured to instruct the remote processor to calculate parameters necessary for overfill protection of the tank; and
d) computer instructions configured to instruct the remote processor to calculate tank overpressure or vacuum parameters in the tank.

12. The marine probe of claim 2, comprising: an external sensor outside of the tank and electrically connected to the probe processor, the external sensor configured to measure ambient pressure and ambient temperature outside the tank, the external sensor providing signals to the probe processor, the probe processor using computer instructions in the probe data storage, the computer instructions configured to instruct the probe processor to compare measured ambient pressure and temperature to measured pressure and temperature inside the tank for gas blanket monitoring and asset protection of the tank.

13. The marine probe of claim 12, comprising computer instructions in the probe data storage, the computer instructions configured to instruct the probe processor to use the plurality of pressure transducers and the plurality of temperature sensors internal to the tank, any temperature sensors and any pressure transducer located in the vapor space of the tank and the external sensor to calculate parameters necessary for emissions monitoring.

14. The marine probe of claim 1, comprising computer instructions in the probe data storage configured to instruct the probe processor to use the plurality of temperature sensors and/or the plurality of pressure transducers to calculate parameters necessary for leak detection and unauthorized movement of fluid into and out of the tank.

15. The marine probe of claim 1, further comprising at least one compound containing sulfur detector in communication with the probe processor for detecting compounds containing sulfur and computer instructions in the probe data storage configured to instruct the probe processor to compute compounds containing sulfur concentration for protection of personnel or for estimation of quality of crude oil, wherein the compound containing sulfur detector is in liquid in the tank, in vapor in the tank or mounted external to the tank.

16. The marine probe of claim 1, wherein the processor housing is weatherproof or explosion proof.

17. The marine probe of claim 1, comprising a plurality of conduits connecting the processor housing with the sensor housings and extending to a bottom of the marine probe.

18. The marine probe of claim 1, comprising computer instructions for instructing the remote processor to use a computed mass of the fluid for balancing during loading and unloading of the floating vessel and for inventory control and custody transfer.

* * * * *